United States Patent [19]

Kanamaru et al.

[11] Patent Number: 5,147,860
[45] Date of Patent: Sep. 15, 1992

[54] TAN-1120, ITS DERIVATIVES, PRODUCTION AND USE THEREOF

[75] Inventors: Tsuneo Kanamaru, Takatsuki; Yukimasa Nozaki, Ikeda; Masayuki Muroi, Suita, all of Japan

[73] Assignee: Takeda Chemical Industries, Ltd., Osaka, Japan

[21] Appl. No.: 447,519

[22] Filed: Dec. 7, 1989

[30] Foreign Application Priority Data

Dec. 27, 1988 [JP] Japan .................. 63-332195
Feb. 20, 1989 [JP] Japan .................... 1-41033
Jul. 10, 1989 [JP] Japan ................... 1-178634

[51] Int. Cl.$^5$ .................. A61K 31/71; C07H 15/252
[52] U.S. Cl. ........................ 514/34; 536/6.4; 536/16.8; 536/16.9; 536/17.2; 435/78
[58] Field of Search ............. 435/78; 514/34; 536/6.4, 16.9, 17.2, 16.8

[56] References Cited

U.S. PATENT DOCUMENTS

| | | | |
|---|---|---|---|
| 4,147,778 | 4/1979 | Umezawa et al. | 536/6.4 |
| 4,749,693 | 6/1988 | Angelucci et al. | 536/6.4 |
| 4,891,360 | 1/1990 | Angelucci et al. | 536/6.4 |
| 4,942,155 | 7/1990 | Cassinelli et al. | 514/34 |
| 4,948,880 | 8/1990 | Hermentin et al. | 536/6.4 |
| 4,987,126 | 1/1991 | Bargiotti et al. | 514/34 |
| 5,049,549 | 9/1991 | Kolar et al. | 514/34 |

FOREIGN PATENT DOCUMENTS

| | | | |
|---|---|---|---|
| 0025713 | 3/1981 | European Pat. Off. | |
| 0026849 | 4/1981 | European Pat. Off. | |
| 0119795 | 9/1984 | European Pat. Off. | |
| 0143323 | 6/1985 | European Pat. Off. | 536/6.4 |
| 0206138 | 12/1986 | European Pat. Off. | |
| 0226173 | 6/1987 | European Pat. Off. | |
| 0239774 | 10/1987 | European Pat. Off. | 536/6.4 |
| 1065134 | 9/1959 | Fed. Rep. of Germany | 536/6.4 |
| 2610557 | 9/1976 | Fed. Rep. of Germany | 536/6.4 |
| 2735455 | 2/1978 | Fed. Rep. of Germany | 536/6.4 |
| 2804099 | 8/1978 | Fed. Rep. of Germany | 536/6.4 |
| 61-50992 | 3/1986 | Japan | 536/6.4 |

OTHER PUBLICATIONS

Uchida et al., The Journal of Antibiotics, vol. 41, pp. 404-408 (1988).
Arcamone et al., Tetrahedron Letters, No. 15, pp. 1007-1010 (1969).
Arcamone et al., J. Am. Chem. Soc., vol. 86, pp. 5334-5336 (1964).
Arcamone et al.; Tet. Lett. 30:3353-3356 (1968).

Primary Examiner—Ronald W. Griffin
Assistant Examiner—Nancy S. Carson
Attorney, Agent, or Firm—Wenderoth, Lind & Ponack

[57] ABSTRACT

The present invention relates to a compound of the formula:

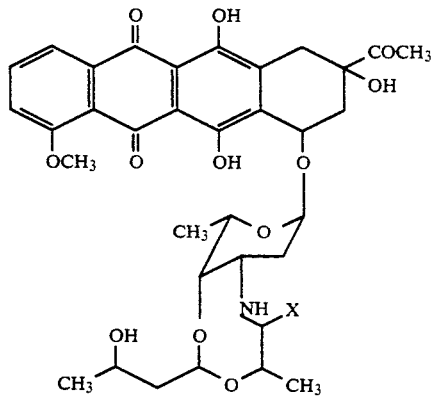

wherein X is hydroxyl group or hydrogen atom, or a salt thereof.

The compound (I) has an acitivity to inhibit angiogenesis, which is useful for prophylaxis and therapy of various diseases accompanying abnormally increased angiogenesis, especially of tumors.

3 Claims, No Drawings

TAN-1120, ITS DERIVATIVES, PRODUCTION AND USE THEREOF

TECHNICAL FIELD

This invention relates to a physiologically active substance TAN-1120 and reduction form thereof, which are effective for prophylaxis and therapy of various diseases accompanying abnormal increase of angiogenesis, a method of preparing them and use of them, and to microorganism therefor.

BACKGROUND TECHNOLOGY

Angiogenesis is known to occur not only in normal physiological events in human and animals such as embryogenesis or ovulation or placentation in the female sexual cycle, but also in repair processes such as wound healing and inflammation, and in various pathological events where rapidly grown and proliferated capillaries damage tissues seriously. Diseases due to such pathological growth of capillaries include diabetic retinopathy, retrolenticular fibroplasia, angiogenesis following kelatoplasty, glaucoma, ocular tumor and trachoma in ophthalmology, psoriasis and purulent granuloma in dermatology, hemangioma and fibrous hemangioma in pediatrics, hypertrophic scar and granulation in surgery, rheumatic arthritis and edematous sclerosis in internal medicine, atherosclerosis in heart diseases, and various tumors.

In particular, abnormally increased angiogenesis in diabetic retinopathy and trachoma causes loss of eye sight in many people, and abnormal angiogenesis in the joint may break cartilage in the joint, inflicting rheumatic arthritis on many patients. Circumstances being such, development of substances has been desired which are useful for treatment and prevention of such diseases accompanying abnormally increased angiogenesis.

And, rapid growth of tumor is considered to be a result of angiogenesis induced by angiogenitic factor produced by tumor cells. Because angiostatic agents are thus expected to be new therapeutic agents against various tumors, studies exploring such agents have started [J. Folkman; Advances in Cancer Research, 43 175, 1985, edited by George Klein and Sidney Weinhouse].

It has already been clarified that heparin or a heparin fragment combined with a so-called angiostatic steroid such as cortisone inhibits angiogenesis [J. Folkman et al.; Science, 221 719 (1983), J. Folkman et al.; Annals of Surgery, 206 375 (1987)].

It has also been reported that a collagen synthesis inhibitor such as L-azetidine-2-carboxylic acid or cis-hydroxyproline, and an inhibitor of collagen proline hydroxylase, or a collagen synthesis inhibitor in combination with $\beta$-cyclodextrin-tetradecasulfate or heparin exerts an angiostatic effect [D. Ingber and J. Folkman; Laboratory Investigation, 59 44 (1988)].

And, it has been pointed out that basement membrane and collagen synthesis in the membrane play an important role in angiogenesis [M. E. Maragoudakis, M. Sarmonika and M. Panoutsacopoulous; J. Pharmacol. Exp. Ther. 244, 729 (1988), D. E. Ingber, J. A. Madri and J. Folkman; Endocrinology, 119, 1768 (1986)].

It has been recognized that fumagillin produced by *Aspergillus fumigatus* known hitherto as an antibiotic and antiprotozoal agent exerts strong angiostatic effect which is potentiated by combination with heparin or $\beta$-cyclodextrin tetradecasulfate [J. Folkman and T. Kanamaru et al.; U.S. patent application Ser. No. 173305, filed on Mar. 25, 1988]. Besides, it has been reported that a steroidal hormone, medroxyprogesterone acetate, which was developed as a synthetic luteal hormone, inhibits angiogenesis induced by various tumors in evaluation of angiogenesis using rabbit corneal micropocket assay [Proceedings of the National Academy of Science, U.S.A 78 1176 (1991)]. And, also with prostaglandin synthesis inhibitors such as Indomethacin, diclofenac sodium, aspirin, etc. [Anticancer Research, 6 251 (1986)] and with anthracene-type anticancer agents such as mitoxantrone, bisantrene, etc. [Biochemical & Biophysical Research Communication, 140 901 (1986)], angiostatic activity is recognized.

And, it has recently been revealed that antirheumatics containing gold, such as gold sodium thiomalate, auranofin, etc. show angiostatic activity, suggesting that at least a part of the antirheumatic action of these compounds is due to their angiostatic action [Journal of Clinic Investigation, 79 1440 (1987), Biochemical & Biological Research Communication, 154 205 (1988)].

In addition to the afore-mentioned non-proteineous angiostatic agents, some proteineous angiostatic agents have been reported such as, cartilage derived factors [Science, 193 70 (1976)], protamine [Nature, 297 307 (1982)], factors derived from human retinal pigment epithelial cells [Arch. Ophthalmol. 103 1870 (1985)] and interferon [Cancer Research, 47 5155 (1987)]. But these are considered to be of little practical use as medicines.

While there have been several reports as described above concerning compounds showing angiostatic activity, the activity is considered to be insufficient for clinical use. Therefore, production of low-molecular and strong angiostatic agents which can be clinically used have been ardently desired.

DISCLOSURE OF THE INVENTION

Based on the background as above, the present inventors isolated a great number of microorganisms in search for new angiostatic agents having stronger activity and less side-effects and found that microorganisms belonging to a certain species produce a novel angiostatic agent. The present inventors recognized that these microorganisms are those of a new species belonging to the genus Streptomyces, that, by cultivating the microorganisms in a proper medium, substances having a strong angiostatic activity can be accumulated in the culture medium and in the cells, and further that stable derivatives thereof can be obtained by subjecting these substances to reduction. The present inventors then isolated these active substances and, on the basis of their physical, chemical and biological properties, proved that they were all new substances. Based on these findings, the inventors made further studies to complete the present invention.

More specifically, the present invention relates to compounds represented by the following general formula (I):

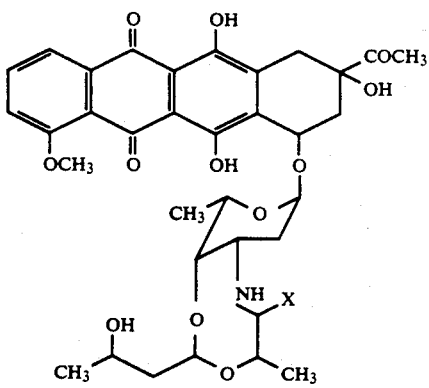

wherein x stands for hydroxyl group (TAN-1120) or hydrogen atom (TAN-1120 reduction form), or salts thereof; a method of producing the compound (I), which is characterized by culturing a microorganism belonging to the genus Streptomyces and being capable of producing the compound (I); provided that X stands for hydroxyl group) in a culture medium, allowing the said compound to be produced and accumulated in the medium, recovering the accumulated compound, then, if desired, subjecting the compound to reduction; an antineoplastic drug comprising a compound described in Claim (1); and *Streptomyces triangulatus* subsp. *angiostaticus.*

As the microorganism producing the physiologically active substance TAN-1120 (hereinafter sometimes called simply as TAN-1120) of the present invention, any one can be employed so long as it belongs to the genus Streptomyces and is capable of producing TAN-1120. For example, the strain *Streptomyces triangulatus* subsp. *angiostaticus* S-14519 strain (hereinafter sometimes called simply called as "S-14519 strain") isolated from the soil collected in Kunisaki peninsula of Ooita Prefecture can be employed for practical use, whose microbiological characteristics are as follows.

The properties of S-14519 strain was examined after the manner described on International Journal of Systematic Bacteriology 16 (3), 313-340 (1960). Unless otherwise indicated, the descriptions are the results after cultivation at 28° C. for 14 days.

(1) Morphological characteristics

Aerial mycelia elongate with simple branching from well elongated and branched vegetative mycelia, and on the top of them are observed zigzag spore chains (usually ten or more) grown from triangular or T-type spores, but no verticils formed. The spores are of the following three types; 1) ellipsoidal and the size is the range of 0.5×0.8–0.7×1.0 μm, 2) triangular and the length of one side is in the range of 0.8–1.1 μm, and 3) T-type or Y-type, and the surfaces are all smooth.

(2) Cultural characteristics on various media

The growth on various media, color of aerial mycelia, color of the reverse of the growth, production of the soluble pigments, color of the soluble pigments, etc. are as shown in Table 1.

(3) Physiological properties a) Growth temperature range (observed for one week using yeast extract-malt extract agar medium): 15° to 33° C.

b) Liquefaction of gelatin: negative c) Hydrolysis of starch: positive d) Coagulation of skimmed milk: negative Peptonization of skimmed milk: negative e) Production of melanoid pigment Tyrosine agar: negative Peptone-yeast extract-iron agar: negative (4) Assimilation of carbon sources (Pridham Gottlieb agar medium)

Assimilability of various carbon sources are as follows.

| Carbon Source | |
|---|---|
| L-arabinose | − |
| D-xylose | − |
| D-glucose | − |
| D-fructose | − |
| Sucrose | − |
| Inositol | + |
| L-Rhamnose | − |
| Raffinose | − |
| D-mannitol | − |
| Control | − |

−: not assimilate
+: assimilate (5) Composition of cell wall 2,6-Diaminopimelic acid in the hydrolysate of whole cell is LL type.

TABLE 1

| No | Culture medium | Growth | Aerial mycelia | Color of reverse | Soluble pigment |
|---|---|---|---|---|---|
| 1 | Sucrose nitrate agar medium | poor | poor, powdery, grayish white | milky white | no |
| 2 | Glucose-asporagine agar medium | moderate | moderate, powdery gray | milky white | no |
| 3 | Glycerine-asparagine agar medium | moderate | moderate, powdery, white to bluish gray | pale-yellowish | no |
| 4 | Slarch-inorganic salt agar medium | moderate | moderate, powdery, white to bluish gray | pale-yellowish | no |
| 5 | Tyrusine agar medium | moderate | poor, white | dark yellowish gray to dark brown | dark brown |
| 6 | Nutrient agar medium | moderate | poor, white | pale yellowish gray | no |
| 7 | Yeast extract-malt extract agar medium | good | good, powdery, bluish pale brown gray | pale brown | no |
| 8 | Oatmeal agar medium | poor | poor, powdery, bluish gray | milky white | no |
| 9 | Peptone-yeast extract-iron agar medium | moderate | poor, white | pale yellowish gray | dark brwn |

Summary of the above-described properties is as follows. The growth of this strain on various synthetic and natural media is colorless to ivory-colored; white to bluish-gray mycelia are formed; the shape of spores is triangular (or Y-type), T-type or ellipsoidal and zigzag spore chains are formed; the surfaces of the spores are smooth; pale dark brown soluble pigment is produced on tyrosine agar medium and peptone-yeast extract-iron agar medium, while no production of melanoid pigment is recognized; and LL-type diaminopimelic acid is contained in cells.

As is clear from the above-described properties, S-14519 strain apparently belongs to genus Streptomyces.

For deciding the taxonomical position of this strain, reference was made to the species described in International Journal of Systematic Bacteriology, Vol. 18 (1968), ibid. Vol. 19 (1969), ibid. Vol. 22 (1972), The Actinomycetes by S. A. Waksman, Vol. 2, (1961), Systematik der Streptomyceten by R. Hütter (1967), Bergey's Manual of Determinative Bacteriology, 8th edition, (1974), etc.

As the result, Streptomyces triangulatus (Annual Research Report of Meiji Seika Kaisha, Ltd., Vol. 13, pp.72–79, 1973) is counted as the strain most closely related to the strain in the present invention. S-14519 strain and a strain of Streptomyces triangulatus (IFO 13799 strain) were cultivated under the same condition, and the cultural characteristics were compared to each other (Table 2). While differences were seen in the observations on the growth on glycerol-asparagine agar medium and tyrosine agar medium, they have many common traits in other respects.

Further, both strains were cultivated at 28° C. for 4 days on a reciprocal shaker employing a same medium, and their productivity of TAN-1120 was compared each other. S-14519 strain showed the remarkable productivity, while no such productivity was observed in IFO 13799 strain. Therefore, the present strain is regarded as a subspecies of Streptomyces triangulatus and named Streptomyces triangulatus subsp. angiostaticus.

The above-mentioned Streptomyces triangulatus subsp. angiostaticus S-14519 strain has been deposited under an accession number of IFO 14801 at Institute for Fermentation, Osaka since Dec. 8, 1988, and also deposited at Fermentation Research Institute, Agency of Industrial Science and Technology, Ministry of International Trade and Industry (FRI, 1-3, Higashi 1-Chome, Tsukuba-Shi, Ibaragi-Ken, Japan) under an accession number of FERM BP-2199 since Dec. 21, 1988 as deposit under the Budapest Treaty.

TABLE 2

| Comparison with an Authentic Known species (growth on various culture media) | | | |
|---|---|---|---|
| | | Streptomyces sp. S-14159 | S. triangulatus IFO 13799 |
| Sucrose-nitrate agar medium | G: | poor, colorless | poor, colorless |
| | AM: | poor, powdery, bluish gray | none |
| | R: | colorless | colorless |
| | SP: | none | none |
| Glucose-asparagine agar medium | G: | moderate, colorless to ivory | poor to moderate |
| | AM: | moderate, powdery, bluish gray | powdery, bluish gray |
| | R: | ivory | pale yellowish gray |
| | SP: | none | none |
| Glycerine-asparagine agar medium | G: | moderate, ivory | poor, limited |
| | AM: | moderate, powdery white to bluish gray | |
| | R: | pale yellowish gray | pale yellowish gray |
| | SP: | none | pale pink |
| Starch-inorganic agar medium | G: | moderate, pale yellowish gray | moderate, dark brown |
| | AM: | moderate, powdery, white to bluish white | moderate, powdery, grayish white to bluish gray |
| Tyrosine agar medium | G: | moderate, dark brown | poor, pale yellowish gray |
| | AM: | poor to medium, powdery, white to bluish gray | none |
| | R: | dark brown to blackish brown | pale yellowish gray |
| | SP: | dark brown | pale pink |

TABLE 2-continued

| Comparison with an Authentic Known species (growth on various culture media) | | | |
|---|---|---|---|
| | | Streptomyces sp. S-14159 | S. triangulatus IFO 13799 |
| Nutrient agar medium | G: | moderate, pale yellowish gray | moderate, pale yellowish gray |
| | AM: | poor to moderate, white | poor, powdery, white to bluish gray |
| | R: | pale yellowish gray | pale yellowish gray |
| | SP: | none | none |
| Yeast extract-malt estract agar medium | G: | good, pale yellowish gray | moderate, pale brown |
| | AM: | good, powdery, bluish-gray | moderate, powdery, bluish gray |
| | R: | yellowish brown | pale yellowish brown |
| | SP: | none | none |
| Peptone-yeast extract | G: | poor, ivory | poor, colorless |
| | AM: | poor to moderate, powdery, white to bluish gray | moderate, powdery, bluish gray |
| | R: | ivory | ivory |
| | SP: | none | no |

G, growth; AM, aerial mycerium; R, color of reverse; SP, soluble pigment

As their common traits, Streptomyces are ready to undergo changes of their properties, for example, various mutants can be readily derived by artificial means such as UV rays, X-rays, chemicals (e.g. nitrosoguanidine, ethyl methansulfonate). Unless the TAN-1120-producing ability is lost, however, any of such mutants can be employed in the practice of this invention.

Examples of the assimilable carbon sources include glucose, maltose, lactose, blackstrap molasses, fats and oils (e.g. soy bean oil, olive oil, etc.), organic acids (e.g. citric acid, succinic acid, gluconic acid, etc.), etc. Examples of digestible nitrogen sources include organic or inorganic nitrogen compounds such as soybean meal, cotton seed meal, corn steep liquor, dry yeast, yeast extract, meat extract, peptone, urea, ammonium sulfate, ammonium nitrate, ammonium chloride, ammonium phosphate, etc. And, examples of inorganic salts generally required for cultivation of Streptomyces include sodium chloride, potassium chloride, calcium carbonate, magnesium sulfate, potassium dihydrogenphosphate, sodium dihydrogenphosphate, etc. and they can be used singly or in a suitable combination. Incorporation of a utilizable sulfur compound, for example, an inorganic sulfur compound such as sulfate (e.g. ammonium sulfate, etc.), thiosulfate (e.g. ammonium thiosulfate, etc.), sulfite (e.g. ammonium sulfite), etc., an organic sulfur compound such as sulfur-containing amino acid (e.g. cysteine, L-thiazoline-4-carboxylic acid), hypotaurine, sulfur-containing peptide (e.g. glutathione), etc., or a mixture of these into a culture medium serves, in some cases, to increase the amount of the desired compound to be produced.

Further, heavy metals such as ferrous sulfate, copper sulfate, vitamins such as vitamin $B_1$, biotin, etc. may be incorporated as occasion demands. An antifoaming agent such as silicone oil, polyalkylene glycol, etc., or a surfactant may also be added to the medium. Other than those components, such organic or inorganic substances as capable of promoting the production of TAN-1120 may further be incorporated in the medium.

Cultivation is conducted in a manner generally employed for the production of antibiotics, and, it may be solid or liquid culture. In the case of liquid culture while any of standing culture, spinner culture, shaking culture and aeration culture can be employed, aerobic shaking culture is preferable. The incubation temperature is preferably maintained around 15° C. to 35° C., more preferably around 24° C. to 28° C., and the pH of medium is in the range of about 4 to 8, more preferably around 6 to 7, and the incubation time ranges from about 8 to 168 hours, preferably from 24 to 144 hours.

Since TAN-1120 thus produced exists in the culture filtrate and cell mass, the culture broth is subjected to centrifugal separation or filtration to separate into the supernatant and cell mass, and can be isolated from the supernatant and the cell mass, respectively. And, depending on cases, it may be more advantageous that an organic solvent such as methanol, acetone, butanol, etc. is directly added to the culture broth to extract the product and purification is conducted therefrom.

For harvesting TAN-1120 from the culture broth, because it is amphoteric fat-soluble substance, a generally employable separation, purification method for recovering such metabolites of microorganisms is conveniently utilized. For example, the method of utilizing difference of solubility between the product and impurities, chromatography using various carriers such as nonionic high porous resin, silica gel, alumina or dextran gel, etc. are utilized singly or in combination.

A practical method of harvesting TAN-1120 accumulated in the culture broth is explained as follows. First, an organic solvent such as methanol, which is capable of dissolving the said compound, is added to the culture broth, and the mixture is stirred to extract the compound, followed by subjecting to filtration by the use of a filter aid such as Hyflo Super Cel.

The filtrate is concentrated to distill off methanol, then the concentrate is made to weakly acid, and extracted with ethyl acetate. The remaining aqueous layer is made neutral and extracted with isobutanol or n-butanol. The butanol layer is washed with dilute aqueous solution of sodium bicarbonate and water, concentrated and dried, then the residue is washed with ether, etc. to obtain a crude oily substance.

This crude substance is repeatedly subjected to extraction with chloroform, and the extract solution is concentrated and dried to leave an oily residue, which is subjected to a silica gel chromatography. As the solvent for development, use is made of, for example, a mixture solvent of chloroform-methanol, preferably a one to which is added a small volume of acetic acid. By gradually increasing the content of methanol in the developer, elution can be performed separating foreign substances.

Fractions containing TAN-1120 thus obtained are further subjected to high performance liquid chromatography to give a purified product of TAN-1120.

Carriers which can be used in such high performance liquid chromatography include reverse phase type resin, for example, YMC-Pack SH-343 ODS (Yamamura Chemical Laboratories, Japan), and, as the solvent system, use is made of a mixture of acetonitrile-acid buffer solution.

Physico-chemical properties of TAN-1120 (free form) obtained in Working Examples to be described hereafter are as follows:

1) Appearance: red to dark red powder.
2) Molecular weight: 671 (by mass spectrum).
3) Molecular formula: $C_{34}H_{41}NO_{13}$.
4) Elemental Analysis: (for $C_{34}H_{41}NO_{13} \cdot H_2O$). Found: C, 58.91; H, 6.08; N, 2.31. Calcd.: C, 59.21; H, 6.28; N, 2.03.

5) Ultraviolet absorption spectrum: $\lambda^{MeOH}_{max}$ ($E^{1\%}_{1cm}$): 234(520), 252(390), 290(125), 477(165), 497(172), 531(115), 576(40).

6) Infrared absorption spectrum (peak by KBr disc, $cm^{-1}$): 3460 to 3480, 2990, 2950, 1720, 1625, 1585, 1450, 1415, 1385, 1360, 1290, 1240, 1210, 1120, 1070, 1035, 1010, 820, 795, 770.

7) $^1H$ NMR spectrum (300 MHz, chemical shift, $\delta$ppm in $CDCl_3$ - $CD_3OD$ (1:2)) 1.21(3 H,d), 1.23(3 H,d), 1.27(3 H,d), 1.75(2 H,m), 1.89(2 H,m), 2.13(1 H,dd), 2.36(1 H,br.d), 2.42(3 H,s), 3.00(1 H,d), 3.15(1 H,m), 3.20(1 H,d), 3.53(1 H,dq), 3.59(1 H,br.s), 3.76(1 H,d), 4.03(1 H,m), 4.09(3 H,s), 4.14(1 H,br.q), 4.72(1 H,t), 5.25(1 H,br.s), 5.49(1 H,br.s), 7.47(1 H,br.d), 7.83(1 H,br.t), 8.03(1 H,br.d) s: singlet, d: doublet, t: triplet, q: quartet, m: multiplet, br: broad.

$^{13}C$ NMR spectrum (75 MHz, $\delta$ppm in $CD_3OD$ - $CDCl_3$ (1:2)): 212.9(s), 187.2(s), 186.9(s), 161.3(s), 156.4(s), 155.6(s), 136.2(d), 135.6(s), 134.5(s), 134.5(s), 120.9(s), 120.0(d), 119.0(d), 111.7(s), 111.5(s), 107.4(d), 101.6(d), 94.3(d), 80.1(d), 79.0(d), 77.0(s), 70.4(d), 65.8(d), 64.7(d), 56.8(q), 44.5(t), 44.3(d), 35.3(t), 33.2(t), 32.3(t), 24.8(q), 23.5(q), 21.1(q), 17.0(q).

9) Specific rotation: $[\alpha]^{23}_D + 230° \pm 15$ (c=0.01, MeOH).

10) Solubility:
Soluble: methanol, chloroform, dimethyl sulfoxide
Hardly soluble: water, n-hexane.

11) Thin-layer chromatography (carrier, silica gel glass plate 60 $F_{254}$, 0.25 mm, E. Merck, W.Germany): Developing solvent: Rf chloroform-methanol-formic acid-water: 0.45 (60:10:1:1).

12) High performance liquid chromatography: Carrier: Cica-Merck LiChrospher, 100 RP-18(e), 5 82 m, (4×125 mm).

Solvent system: 40% acetonitrile - 0.02M phosphate buffer solution (pH 3.0).
Flow rate: 1 ml/minute.
Retention time ($t_R$): 4.03 minutes.

From the physical and chemical data of, among others, UV spectrum, TAN-1120 is identified as a compound belonging to anthracyclines (I: wherein X=hydroxyl group), and, since TAN-1120 has, as a partial structure, carbinolamine

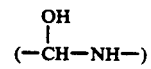

structure, it readily changes into imine (—CH=N—) type or aldehyde-amine type, and it can be present as a mutually changeable equilibrium mixture, and these tautomeric isomers and dehydrated forms are also included in the present invention.

More specifically, TAN-1120 is unstable in that it undergoes mutual changes into compounds whose carbinolamine moiety is imine form or ring-opened form (aldehyde-amine form), but, under certain conditions, it can be isolated as carbinol-amine form. Usually, however, TAN-1120 is present as an equbrium mixture of compounds assumed as carbinol-amine form, imine form and ring-opened form (aldehyde-amine form).

The physiologically active TAN-1120 reduction form can be produced by subjecting TAN-1120 to reduction, using as a reducing agent, metal boron hydrides e.g. sodium cyanoborohydride. The reaction is conducted in a solvent such as acetonitrile, tetrahydrofuran, dioxane, dimethoxy-ethane, methanol, ethanol, methylene chloride, chloroform, water, etc., and, depending on the reducing agent employed, the reaction is conducted preferably under acid conditions.

The reaction is carried out at temperatures ranging from $-80°$ C. to $+80°$ C. for a period ranging from one minute to 48 hours. While taking reaction conditions such as reducing agents, solvents, etc. into consideration, the state of proceeding of the reaction can be controlled by observing the reaction state by means of, for example, a thin-layer chromatography.

The reaction affords generally a mixture, and, for isolating the said compound, use is made of a purification process employed for preparation of anthracycline compounds. For example, various chromatography using silica gel, adsorptive synthetic resin, dextran gel, etc. and means of utilizing the differences of solubility in organic solvents can be employed singly or in combination.

Physical and chemical properties of the thus-obtained TAN-1120 reduction form (free form) are as follows:

1) Appearance: red to dark reddish powder.
2) Molecular weight: 655 (by mass spectrum).
3) Molecular formula: $C_{34}H_{41}NO_{12}$.
4) Specific rotation: $[\alpha]^{22}_D +184°$ (c=0.08, $CHCl_3$).
5) $\lambda^{MeOH}_{max}$ ($E^{1\%}_{1\,cm}$): 233(550), 251(415), 287(132), 476(174), 495(180), 530(122), 575(45).
6) Infrared absorption spectrum (peak by KBr disc method, $cm^{-1}$): 3450, 2980, 2940, 1720, 1620, 1580, 1410, 1375, 1350, 1290, 1235, 1210, 1115, 1030, 1000, 820, 790, 765.
7) $^1H$ NMR spectrum (300 MHz, chemical shift in $CDCl_3$ $\delta$ppm): 1.10(3 H,d), 1.24(3 H,d), 1.28(3 H,d), 1.60(1 H,m), 1.78(1 H,m), 1.94(2 H,m), 2.09(1 H,dd), 2.32(1 H,br.d), 2.41(3 H,s), 2.66(1 H,dd), 2.77(1 H,dd), 2.84(1 H,m), 2.97(1 H,d), 3.24(1 H,dd), 3.54(1 H,br.s), 3.80(1 H,m), 4.08(3 H,s), 4.12(2 H,m), 4.67(1 H,t), 4.76(1 H,br.), 5.30(1 H,br.s), 5.49(1 H,br.d), 7.39(1 H,dd), 7.78(1 H,dd), 8.03(1 H,dd), 13.31(1 H,br), 13.95(1 H,br.s) s, d, t, q, m, br are of the same meaning as defined above.
8) $^{13}C$ NMR spectrum (75 MHz, chemical shift in $CDCl_3$ $\delta$ppm): 211.6(s), 187(s), 186.8(s), 161.1(s), 156.4(s), 155.8(s), 135.6(d), 135.6(s), 134.3(s), 134.2(s), 121.0(s), 119.8(d), 118.4(d), 111.4(s), 111.3(s), 107.2(d), 101.2(d), 79.6(d), 77.6(d), 76.9(s), 69.5(d), 65.7(d), 64.6(d), 56.7(q), 52.8(t), 51.6(d), 44.0(t), 34.9(t), 33.5(t), 32.5(t), 24.7(q), 23.4(q), 22.0(q), 17.0(q).

In the said compound obtained by reduction, mutually convertible function groups, i.e. carbinolamine←imine←aldehyde-amine, observed in the starting physiologically active substance TAN-1120 are lost.

More concretely stating, the double bond of imine (—CH=N—) is saturated to become —$CH_2$—NH—, thus being stabilized, and, in the structure of the other portions, no change is seen from that of TAN-1120.

The compound (I) can be formed into an acid addition salt thereof by a per se conventional method. The salts are exemplified by those with an inorganic acid such as hydrochloric acid, sulfuric acid, phosphoric acid, etc., and those with an organic acid such as formic acid, acetic acid, propionic acid, maleic acid, citric acid, succinic acid, tartaric acid, etc., which are all physiologically acceptable ones.

The compound (I) showing a strong angiostatic activity is remarkably useful as a prophylactic and therapeutic agent against various diseases caused by abnormally increased angiogenesis described in the foregoing. And, antineoplastic activity based on strong angiostatic action is also expected.

The said compound is administered orally or parenterally to mammals (e.g. rat, rabbit, monkey and human) in the form of tablet, granule, capsule, syrup, powder, injection, cream or ointment for local application, or eye drop. Pharmaceutical compositions used together with the active substance for production of the preparations of various drug forms may contain appropriate additives (materials for preparations) such as excipients, binders, disintegrators, lubricants, coloring agent, flavoring agent, stabilizers, etc. The preparations may be administered after processing into sustained release preparations using sustained release polymers, etc. For example, the preparations are incorporated in ethylene vinyl acetate copolymer pellets which are then implanted surgically into the tissues to be treated.

For example, for treatment of tumors or diabetic retinopathy, compositions containing a pharmaceutically acceptable carrier are given orally or by intravenous injection. More concretely, the dose is determined according to the patient and the pathological state to be treated, and is desirably given orally or non-orally at a daily dose of 10 $\mu$g to 10 mg divided into 2 to 3 times. The compound (I), in such dosage as above, shows no serious toxicity. For treatment of the above-mentioned retinopathy and trachoma, the compound (I) is given in the form of eyedrops as well once to four times a day according to the state of the patient.

Angiostatic activity was measured by the shellless chick chorioallantoic membrane (CAM) assay, reported by J. Folkman et al. [R. Crum et al: Science 230 1375 (1985)] with slight modifications. In brief, a chick embryo obtained by breaking a shell of a fertilized egg which had been cultivated for three days was hung in a hammock of polyvinylidene chloride film in a plastic cup and subjected to sterile culture for further 5 days.

The test sample was prepared as follows: A methanol solution of a compound of this invention prepared aseptically and an aqueous solution of 1% methyl cellulose were mixed in an equal volume. Ten $\mu$l of the mixture was gently added dropwise onto a Teflon plate, and air-dried under sterile condition to give a methyl cellulose disk of about 4 mm in diameter containing the test sample. Onto the chorioallantoic membrane cultivated for 5 days after shell-breaking, the methyl cellulose disk prepared as described above was placed gently, and the culture of the embryo was continued under sterile conditions. Twenty-four and 48 hours later, an avascular zone formed around the disk was examined microscopically ($\times20$, SMZ-10, Nikon). Angiostatic activity was calculated by dividing the number of the disks giving avascular zones by the number of disks tested. As shown in Table 3, the compounds of this invention were found to have remarkably strong angiostatic activity.

TABLE 3

| Compound | Amount of Sample ng/disk | Angiostatic Activity* (%) |
| --- | --- | --- |
| TAN-1120 | 0.03 | 25 |
|  | 0.1 | 100 |
|  | 0.3 | 100 |
|  | 1 | 92 |
|  | 3 | 100 |
| TAN-1120 reduction form | 0.1 | 0 |
|  | 1 | 22 |
|  | 10 | 80 |

*Values measured after 48 hours

EXAMPLES

The following Examples will describe the present invention in more detail.

EXAMPLE 1

A seed culture medium (500 ml, pH 7.0) consisting of glucose 2%, soluble starch 3%, corn steep liquor 1%, raw soybean flour 1%, peptone 0.5%, sodium chloride 0.3%, calcium carbonate, precipitated 0.5% in a 2-liter Sakaguchi flask was sterilized at 120° C. for 20 minutes. The medium was inoculated with *Streptomyces triangulatus* subsp. *angiostaticus* S-14519 (IFO 14801, FERM BP-2199), followed by subjecting to reciprocal shaking culture at 28° C. for 48 hours. The whole culture thus obtained was transferred to a seed culture medium (30 liters) described above in a 50-liter fermentor, followed by subjecting to culture with aeration (30 l/minute) and agitation (280 rpm) at 28° C. for 48 hours.

The whole culture thus obtained was transferred to a fermentation medium (pH 7.0, 100 liters) consisting of glucose 5.5%, corn gluten meal 3.5% and calcium carbonate, precipitated 0.7% in a 200-liter tank, followed by subjecting to aerobic culture with aeration (100 l/min.) and agitation (150 rpm) at 28° C. for 90 hours, to obtain culture broth (90 liters).

EXAMPLE 2

The culture broth (90 liters) obtained in Example 1 was made pH 6.6, to which was added methanol (180 liters), and the mixture was stirred for 30 minutes, followed by subjecting to filtration by using Hyflo Super Cel (Johns-Manville Inc., U.S.A.) as the filter aid.

This filtrate (244 liters) was concentrated under reduced pressure, and methanol was distilled off. The pH of the residue was made to 5.0 and washed twice with 20 liters each portion of ethyl acetate, then the pH of the remaining aqueous layer was made to 7.0, followed by extraction twice with 7.5 liters each portion of i-butanol.

The i-butanol layer (13 liters) was washed twice with a 2% aqueous solution of NaHCO$_3$ (3 liters), twice with water (6 liters), successively, followed by concentration to dryness under reduced pressure. The oily residue was washed with diethyl ether (500 milliliters). To the residue insoluble in ether was added chloroform (500 milliliters), and the mixture was subjected to extraction three times. The chloroform extracts were combined and concentrated to leave 2.3 g of an oily residue.

This oily residue was dissolved in chloroform, which was poured onto a silica gel (E. Merck, the Federal Republic of Germany) column to allow the compound of this invention to be adsorbed on the column, followed by developing with chloroform (1 liter) containing 1% acetic acid, chloroform (1 liter) containing 1% methanol and 1% acetic acid, chloroform (3 liters) containing 2% methanol and 1% acetic acid and chloroform (1 liter) containing 5% methanol and 1% acetic acid successively.

Active fractions were combined, washed with 2% aqueous solution of NaHCO$_3$, followed by concentration to give a powdery residue (430 mg). One hundred and fifty mg of the residue was subjected to high performance liquid chromatography, divided into three parts, for purification.

Fractionation (10 ml each) was carried out by using a column of YMC-pack SH-343 ODS (Yamamura Chemical Laboratories, Japan), 40% acetonitrile - 0.05 M phosphate buffer solution (pH 3.0) as mobile phase at the flow rate of 10 ml/minute. Fractions No.12 and No.13 (60 ml in total) were combined and concentrated. The pH of the concentrate (25 ml) was adjusted to 7.2, then extraction was carried out twice with chloroform (15 ml). Chloroform layers were combined and washed with water (15 ml), to which was added methanol, followed by concentration to give TAN-1120 (14.5 mg) as dark reddish powder.

EXAMPLE 3

The physiologically active substance TAN-1120 (20 mg) was dissolved in a mixture of acetonitrile - 0.05M phosphate buffer solution (pH 3.0) (2:1, 5 ml). To the solution was added, while stirring under ice-cooling, sodium cyanoborohydride (5 mg).

The mixture was stirred for further 15 minutes under ice-cooling. To the reaction mixture was added water (10 ml), and its pH was adjusted to 9.5, followed by extraction with chloroform (25 ml). The chloroform layer was washed with water and concentrated. The concentrate was subjected to a silica gel thin-layer chromatography (Merck, PLC plate, silica gel 60F$_{254}$, 2 mm thick), followed by development with a mixture of chloroform - methanol (9:1).

Bands showing Rf 0.65 were scraped off and eluted with chloroform-methanol (2:1), followed by concentration to give the corresponding derivative (9.5 mg) as red powder.

What is claimed is:

1. A method for the treatment of a disease caused by abnormally increased angiogenesis in a mammal, which comprises administering to mammal in need of such treatment an angiostatic effective amount of a compound of the formula:

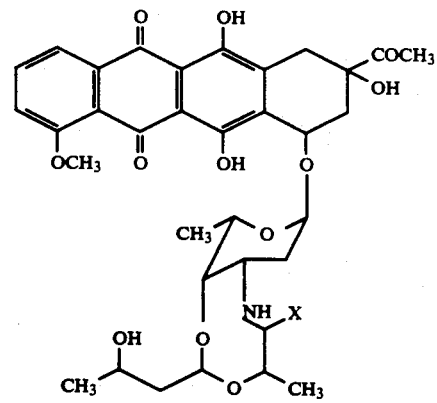

wherein X is hydroxyl group or hydrogen atom, or a pharmaceutically acceptable salt thereof.

2. A method according to claim 1 wherein X is the hydroxyl group.

3. A method according to claim 1 wherein X is hydrogen.

UNITED STATES PATENT AND TRADEMARK OFFICE
CERTIFICATE OF CORRECTION

PATENT NO. : 5,147,860                    Page 1 of 2
DATED      : September 15, 1992
INVENTOR(S): TSUNEO KANAMARU, YUKIMASA NOZAKI and MASAYUKI MUROI It is certified that error appears in the above-indentified patent and that said Letters Patent is hereby corrected as shown below:

Column 1, line 44, change "43" to read "43";
         line 49, change "221" to read "221";
         line 50, change "206" to read "206";
         line 57, change "59" to read "59";
         line 62, change "244" to read "244";
         line 63, change "119" to read "119".

Column 2, line 10, change "78" to read "78"; change "1991" to —1981—;
         line 13, change "6" to read "6";
         line 15, change "140" to read "140";
         line 24, change "79" to read "79";
         line 25, change "154" to read "154";
         line 30, change "193" to read "193"; change "297" to "297";
         line 32, change "103" to read "103";
         line 33, change "47" to read "47".

Column 3, line 45, change "16" to read "16"; change "1960" to —1966—.

UNITED STATES PATENT AND TRADEMARK OFFICE
CERTIFICATE OF CORRECTION

PATENT NO. : 5,147,860
DATED : September 15, 1992
INVENTOR(S) : TSUNEO KANAMARU, YUKIMASA NOZAKI and MASAYUKI MUROI It is certified that error appears in the above-indentified patent and that said Letters Patent is hereby corrected as shown below:

Column 5, in Table 2, at line 55, immediately below "poor, limited" insert —none—;

at line 63, immediately above "G: moderate, dark    poor, pale yellowish" insert the following
—R: pale yellowish brown    pale dark brown
 SP: none                    none—.

Signed and Sealed this

Twentieth Day of December, 1994

BRUCE LEHMAN

Attesting Officer            Commissioner of Patents and Trademarks